(12) United States Patent
Montiel et al.

(10) Patent No.: US 7,183,430 B2
(45) Date of Patent: Feb. 27, 2007

(54) COMPOUNDS WHICH CAN BLOCK THE RESPONSE TO CHEMICAL SUBSTANCES OR THERMAL STIMULI OR MEDIATORS OF INFLAMMATION OF NOCICEPTORS, PRODUCTION METHOD THEREOF AND COMPOSITIONS CONTAINING SAME

(75) Inventors: Antonio Ferrer Montiel, Alicante (ES); Asia Fernández Carvajal, Alicante (ES); Carolina Garcia Martínez, Alicante (ES); Carlos Belmonte Martínez, Alicante (ES); Wim Van Den Nest, Barcelona (ES); Cristina Carreño Serraïma, Barcelona (ES)

(73) Assignee: Diverdrugs, S.L. (ES)

( * ) Notice: Subject to any disclaimer, the term of this patent is extended or adjusted under 35 U.S.C. 154(b) by 131 days.

(21) Appl. No.: 10/515,459

(22) PCT Filed: May 16, 2003

(86) PCT No.: PCT/ES03/00218

§ 371 (c)(1),
(2), (4) Date: Feb. 7, 2005

(87) PCT Pub. No.: WO03/097670

PCT Pub. Date: Nov. 27, 2003

(65) Prior Publication Data

US 2005/0130907 A1   Jun. 16, 2005

(30) Foreign Application Priority Data

May 20, 2002   (ES) ................................ 200201142

(51) Int. Cl.
C07C 233/05      (2006.01)
A61K 31/165      (2006.01)

(52) U.S. Cl. ...................... 564/153; 562/444; 562/445; 562/448; 514/563; 514/616

(58) Field of Classification Search ............... 562/444, 562/445, 448; 564/153; 514/563, 616
See application file for complete search history.

(56) References Cited

FOREIGN PATENT DOCUMENTS

WO    WO 02/30956 A1    4/2002

OTHER PUBLICATIONS

Carolina Garcia-Martinez, et al. "Attenuation of thermal nociception and hyperalgesia by VR1 blockers" *PNAS*, vol. 99, No. 4, Feb. 19, 2002, pp. 2374-2379.

Jacqueline A. Gibbons, et al. "Pharmacologic Characterization of CHIR 2279, an N-Substituted Glycine Peptoid wtih High-Affinity Binding for $\alpha_1$-Adrenoceptors", *Journal of Pharmacology and Experimental Therapeutics*, vol. 277, No. 2, 1996, pp. 885-899.

John A. W. Kruijtzer, et al. "Solid-Phase Syntheses of Peptoids using Fmoc-Protected N-Substituted Glycines: The Syntheses of (Retro) Peptoids of Leu-Enkephalin and Substance P" *Chem. Eur. J.* 1998, No. 8, pp. 1570-1580.

Humet, M., et al., "A Positional Scanning Combinatorial Library of Peptoids As a Source of Biological Active Molecules: Identification of Antimicrobials", *J. Comb. Chem.*, 5:597-605 (2003).

*Primary Examiner*—Shailendra Kumar
(74) *Attorney, Agent, or Firm*—Ostrolenk, Faber, Gerb & Soffen, LLP

(57)   ABSTRACT

The invention relates to compounds having formula (I), which can block the response to chemical substances or thermal stimuli or mediators of inflammation of nociceptors, a production method thereof and compositions containing same. According to the invention, Ar is a phenyl group substituted with one or more halogen groups; $R_1$ is amino, hydroxyl or thiol, all of which may or may not be substituted with formula (II) or with aliphatic or cyclic groups; $R_2$ is H or an alkyl, aryl, aralkyl or acyl group or formula (III); $R_3$ is H or formula (IV); $R_4$ and $R_6$ are H or an aliphatic or cyclic group; $R_5$ is H or formula (V); $R_7$ is H or an aliphatic or cyclic group; Z is amino, hydroxyl or thiol, all of which may or may not be substituted with aliphatic or cyclic groups; W is a linkage or formula (VI); X is a linkage or formula (VII); Y is amino which may or may not be substituted with formula (VIII) or an alkyl, aryl, aralkyl or acyl group; m, q and s can vary between 1 and 9 and n and p can vary between 1 and 10

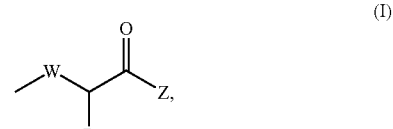

(I)

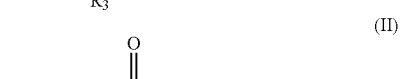

(II)

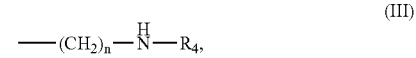

(III)

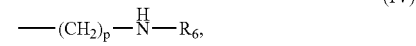

(IV)

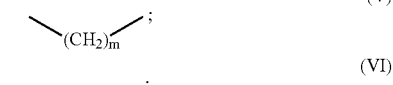

(V)

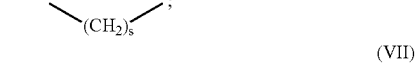

(VI)

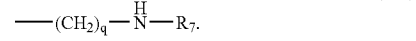

(VII)

63 Claims, No Drawings

COMPOUNDS WHICH CAN BLOCK THE RESPONSE TO CHEMICAL SUBSTANCES OR THERMAL STIMULI OR MEDIATORS OF INFLAMMATION OF NOCICEPTORS, PRODUCTION METHOD THEREOF AND COMPOSITIONS CONTAINING SAME

CROSS-REFERENCE TO RELATED APPLICATIONS

The present application is a 35 U.S.C. § 371 national phase conversion of International Application No. PCT/ES03/00218 filed May 16, 2003, which claims priority of Spanish Application No. P200201142. filed May 20, 2002.

FIELD OF THE INVENTION

This invention refers to compounds capable to block the response to chemical substances or thermal stimuli or nociceptor inflammation mediators, preferably by means of the attenuation and/or interference of the molecular mechanisms responsible for nociceptor sensitization, to a method for the obtainment thereof, and to compositions containing said compounds useful in the treatment of diseases or disorders mediated by the activity of said nociceptors, for example, pain sensations.

BACKGROUND OF THE INVENTION

Pain is a serious social and economic problem. It is calculated that more than 2 million persons are disabled every day due to suffering from temporary or chronic painful sensations. Clear examples are algesia experienced by patients with cancer, headache, arthritis, burns, injured patients and those surgically operated. Despite the severity of the problem, the pharmacological arsenal for controlling, preventing and/or reducing its symptoms and progress is surprisingly limited, partly due to the lack of specific target therapies.

Pain sensation begins when the peripheral terminals of a group of sensory neurons, known as nociceptor neurons, are activated by harmful chemical, mechanical or thermal stimuli (1, 2) [see the section relating to the LITERATURE]. Nociceptor neurons transmit the information about the tissue damage to the centers processing the pain sensation in the spinal cord and the brain.

Although the biological mechanisms necessary for pain transmission are not clearly established, it has been shown that the inflammation mediator compounds such as, for example, the neuronal growth factor and bradykinin, sensitize nociceptors decreasing their response threshold to harmful chemical, thermal and mechanical stimuli. The sensitization process seems to be mediated by the activation of intracellular signaling pathways leading to the modulation of the membrane receptors responsible for the integration of harmful stimuli. For example, it has been described that ion channels present on the nociceptor surface such as vanilloid receptor I, sodium channels, ionotropic glutamate receptors and purinergic receptors are actively modulated by pro-algesic agents. Accordingly, a strategy to reduce peripheral pain transmission and sensation is to act by reducing the pro-algesic sensitization of the nociceptors by means of developing chemical compounds which specifically interact on excitatory mechanisms and/or molecules and increase the response thresholds of the nociceptors.

Despite the progress carried out in the last years, specific analgesic compounds decreasing the pro-algesic sensitization of the nociceptors and therefore, aiding to alleviate painful sensations of the inflammatory process, had yet not been developed. The effort carried out up to date has largely consisted on developing opioids recognizing the opioid receptors of the central nervous system (1, 2). Although strong analgesics, these molecules show important side effects, such as addiction, tolerance, cognitive anomalies, etc., which limit their clinical use (3, 4). Likewise, a great investment has been carried out in the development of non-steroidal anti-inflammatory compounds. Although effective in the treatment of pain, these molecules have limitations, side effects and toxicology hindering their use, especially in chronic inflammatory pain. An important effort to develop competitive and non-competitive glutamate and/or glycine [a co-agonist participating in the activation of the N-methyl-D-aspartate activated glutamate receptor (NMDA)] antagonists has also been carried out. These inhibitors have been shown to be effective and powerful mitigating the pain sensation, but have shown a limited clinical utility again due to the cognitive-type side effects they show (5).

Therefore, there is still a need for searching for products capable to reduce and/or treat the peripheral pain sensation, overcoming the previously mentioned drawbacks.

SUMMARY OF THE INVENTION

A strategy for searching for products capable to reduce and/or treat the peripheral pain sensation, overcoming the previously mentioned drawbacks, is the identification of molecules preferably acting on sensitized nociceptors, attenuating their sensitization.

In this respect, the present invention provides a solution to the mentioned need, comprising the development of compounds capable to block the response to chemical substances and thermal stimuli or nociceptor inflammation mediators. Analyses carried out to determine the action mechanism show that they preferably act by inhibiting the vanilloid receptors and show a marginal activity on the NMDA receptor and the neuronal calcium channels.

Therefore, a first aspect of this invention refers to a compound according to general Formula (I) detailed below, capable to block the response to chemical substances or thermal stimuli or nociceptor inflammation mediators.

A second object of the invention refers to a method for preparing said compound by using a solid-phase strategy.

An additional aspect of this invention refers to a composition comprising said compound, such as a pharmaceutical composition or a cosmetic composition.

Another aspect of the invention refers to the use of the compound of general Formula (I) in the production of a composition, either pharmaceutical or cosmetic.

DETAILED DESCRIPTION OF THE INVENTION

According to a first aspect, the invention provides a compound of general Formula (I),

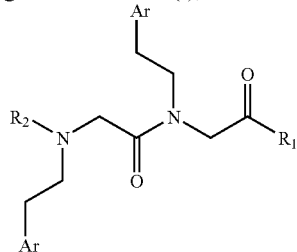

its stereoisomers and mixtures thereof, racemic or not, and the pharmaceutically acceptable salts thereof, wherein Ar is a phenyl group substituted with one or more halogen groups;

$R_1$ is amino, hydroxyl or thiol, all of them substituted or not with

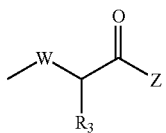

or aliphatic or cyclic groups;

Z is amino, hydroxyl or thiol, all of them substituted or not with aliphatic or cyclic groups;

W is a bond or

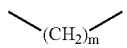

m can range between 1 and 9;

$R_3$ is H or

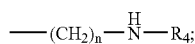

n can range between 1 and 10;

$R_4$ is H, or an aliphatic or cyclic group;

$R_2$ is H or an alkyl, aryl, aralkyl or acyl group or

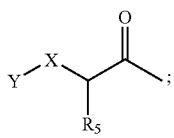

X is a bond or

s can range between 1 and 9:

$R_5$ is H or

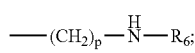

p can range between 1 and 10;

$R_6$ is H, or an aliphatic or cyclic group;

Y is amino, substituted or not with

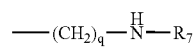

or an alkyl, aryl, aralkyl or acyl group;

q can range between 1 and 9;

and $R_7$ is H, or an aliphatic or cyclic group.

Preferred structures of the compounds shown in Formula (I) are those where

Ar is a 2,4-dichlorosubstituted phenyl group $R_4$ and $R_6$ are independently H or

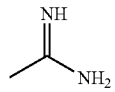

The compounds of the present invention can exist as stereoisomers or mixtures of stereoisomers; for example, if there are one or more asymmetrical carbons, they can have a (R)-, (S)- or (R, S)-configuration, independently from one another. Therefore, it is possible to obtain isomeric as well as racemic mixtures or diastereomeric mixtures, or pure diastereomers or enantiomers, depending on the number of asymmetrical carbons and whether isomers or isomeric mixtures are present. Preferred structures of the compounds of Formula (I) are pure isomers (enantiomers or diastereomers).

Within the context of the present invention, the term "aliphatic group" refers to a saturated or unsaturated linear or cyclic hydrocarbon group. The term "hydrocarbon group" is used for covering, for example, alkyl, alkenyl and alkynyl groups. The term "alkyl group" refers to a saturated linear or branched hydrocarbon group, including, for example, methyl, ethyl, isopropyl, isobutyl, t-butyl, heptyl, dodecyl, octadecyl, amyl, 2-ethylhexyl, 2-methylbutyl, 5-methylhexyl and the like. The term "alkenyl group" refers to an unsaturated linear or branched hydrocarbon group with one or more double carbon-carbon bonds, such as the vinyl group. The term "alkynyl group" refers to a linear or branched unsaturated hydrocarbon group with one or more triple carbon-carbon bonds. The term "cyclic group" refers to a closed hydrocarbon ring, which can be classified as an alicyclic, aromatic or heterocyclic group. The term "alicyclic group" refers to a cyclic hydrocarbon group with properties similar to aliphatic groups. The term "aromatic group" or "aryl group" refers to a mono or polycyclic aromatic hydrocarbon group. The term "heterocyclic group" refers to a closed hydrocarbon ring, in which one or more than one of the atoms of the ring is an element other than carbon (for example, nitrogen, oxygen, sulfur . . . ).

As is understood in this technical field, a high degree of substitution is not only tolerated, but also recommended. Therefore, substitution in the compounds of the present invention can exist. For the purpose of simplifying the present description of the invention, the terms "group" and "block" will be used to differentiate between chemical species which allow substitution or which can be substituted, and those which do not allow substitution or which cannot be substituted. In this manner, when the term "group" is used for describing a chemical substituent, the described chemical material includes both the unsubstituted group and the one containing the O, N or S atoms. On the other hand, when the term "block" is used to describe a chemical compound or substituent, only unsubstituted chemical material can be included. For example, the expression "alkyl group" will not only include open chain saturated alkyl substituents, such as methyl, ethyl, propyl, isobutyl and the like, but also alkyl substituents containing other substituents known in the state of the art, such as hydroxy, alkoxy, amino, carboxyl, carboxamido, halogen, cyano, nitro, alkylsulfonyl atoms and others. Therefore, "alkyl group" includes ether, haloalkyl, alcohol, thiol, carboxyl, amine, hydroxyalkyl, sulfoalkyl, guanidine groups, and other ones. On the other hand, the expression "alkyl block" is limited only to inclusion of open chain saturated alkyl substituents, such as methyl, ethyl, propyl, isobutyl and the like.

Within the scope of the present invention, pharmaceutically acceptable salts of the compounds of Formula (I) provided by this invention are included. The term "pharmaceutically acceptable salts" includes the salts usually used to form metal salts or acid addition salts. The nature of the salt is not crucial, as long as it is pharmaceutically acceptable. Pharmaceutically acceptable salts of the compounds of Formula (I) can be obtained from organic or inorganic acids. Said salts can be obtained by standard methods, well known in the state of the art.

Additionally, the compounds of the invention can undergo reversible modifications for the purpose of increasing their bioavailability and ability to pass the blood-brain barrier and epithelial tissue.

The synthesis of the compounds of general Formula (I) can be carried out according to standard methods known in the state of the art, such as for example the adaptation of the solid phase peptide or peptoid synthesis methods (6–10), solution synthesis or a combination of solid phase and solution synthesis methods.

For example, a method for obtaining the compounds of general Formula (I) is that in which a fragment of the compound of general Formula (I) having a free carboxyl group or a reactive derivative thereof, is reacted with a complementary fragment, having an amino group, with at least one free hydrogen atom, with the resulting formation of an amide bond, and in which said fragments have functional groups which do not participate in the formation of the amide bond, if any, which are conveniently protected with temporary or permanent protective groups.

Another example of method for obtaining the compounds of general Formula (I) is that in which a fragment of the compound of general Formula (I) having a leaving group, such as tosyl group, mesyl group and halogen groups among others, is reacted with a complementary fragment having an amino group with at least one free hydrogen atom by means of a nucleophilic substitution reaction, and where said fragments have functional groups which do not participate in the formation of the N—C bond, if any, which are conveniently protected, with temporary or permanent protecting groups. Examples of protecting groups, their introduction and their elimination, can be found disclosed in the literature (11, 12). The term "protecting groups" also includes the polymeric supports used in the solid phase synthesis.

When the synthesis is completely or partially carried out in solid phase, polystyrene, polyethylenglycol grafted in polystyrene and the like can be mentioned as solid supports to be used in the method of the invention, as for example p-methylbenzhydrylamine (MBHA) resins (13), 2-chlorotrityl resins (14), TentaGel® resins and the like, which can include a labile spacer or not, such as 5-(4-aminomethyl-3, 5-dimethoxyphenoxy) valeric acid (PAL) (15), 2-[4-aminomethyl-(2,4-dimethoxyphenyl)phenoxyacetic acid (AM) (16), Wang (17) and the like, allowing the simultaneous deprotection and separation of the polymeric support compound.

According to that set forth previously, a series of preferred embodiments for preparing the compounds of Formula (I) are detailed below, with no limiting sense for the invention.

According to a first embodiment, a compound of Formula (I) can be prepared, where $R_1$ is amino, hydroxyl or thiol, all of them substituted or not with aliphatic or cyclic groups;

$R_2$ is

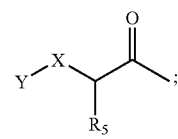

X is a bond;

$R_5$ is

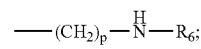

p can range between 1 and 10;

$R_6$ is H, or an aliphatic or cyclic group;

Y is an amino group, substituted or not with an alkyl, aryl, aralkyl or acyl group;

in accordance with a process comprising the following sequential steps:

(a) incorporating a unit of haloacetic acid by means of a coupling agent, such as for example a carbodiimide and the like, on a solid support which can contain an acid-labile spacer to form an amide, ester or thioester bond, (b) halogen shift by nucleophilic substitution with an ethylamine, substituted in position 2 with a phenyl group, which can be substituted by one or more halogen groups, in the presence of a tertiary amine, such as for example triethylamine (TEA), diisopropylethylamine (DIEA) and the like.

(c) incorporating a unit of haloacetic acid by means of a coupling agent, such as for example a carbodiimide or the like.

(d) halogen shift by nucleophilic substitution with an ethylamine, substituted in position 2 with a phenyl group, which can be substituted by one or more halogen groups in the presence of a tertiary amine, such as for example TEA, DIEA and the like.

(e) by means of Fmoc strategy, incorporating a unit of $N^\alpha$-Fmoc-amino acid of general structure

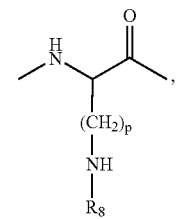

where $R_8$ is a protective group protecting the amino group, as for example tert-butoxycarbonyl (Boc), Mtt (4-methyltrityl) and the like, and where p is 1 to 10, as for example $N^\alpha$-Fmoc-$N^\beta$-Boc-2,3-diaminopropionic acid, $N^\alpha$-Fmoc-$N^\epsilon$-Boc-lysine, $N^\alpha$-Fmoc-$N^\delta$-Boc-ornithine and the like; or where $R_8$ is a group

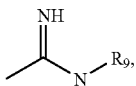

where $R_9$ is a guanidine protecting group, for example 2,2,5,7,8-pentamethylchroman-6-sulphonyl (Pmc), 2,2,4,6,7-pentamethyl-dihydrobenzofuran-5-sulphonyl (Pbf) and the like and p is 1 to 10, for example $N^\alpha$-Fmoc-$N^g$-Pbf-arginine, $N^\alpha$-Fmoc-$N^g$-Pmc-homoarginine and the like.

(f) eliminating the Fmoc group with usual reactants in peptide synthesis.

(g) alkylating or acylating the generated free amino function, if necessary;

(h) releasing the compound from the resin in the acid medium.

According to a second embodiment, a compound of Formula (I) can be prepared, wherein $R_1$ is amino, hydroxyl or thiol, all of them substituted or not with aliphatic or cyclic groups;

$R_2$ is

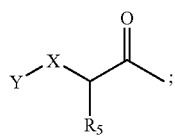

$R_5$ is H;

X is

s is 1 to 9;

Y is an amino group, substituted or not with an alkyl, aryl, aralkyl or acyl group;

in accordance with a process comprising the following sequential steps:

(a) incorporating a unit of haloacetic acid by means of a coupling agent, such as a carbodiimide and the like, on a solid support which can contain an acid-labile spacer to form an amide, ester or thioester bond, (b) halogen shift by nucleophilic substitution with an ethylamine, substituted in position 2 with a phenyl group, which can be substituted by one or more halogen groups, in the presence of a tertiary amine, as for example TEA, DIEA, and the like.

(c) incorporating a unit of haloacetic acid by means of a coupling agent, such as a carbodiimide and the like.

(d) halogen shift by nucleophilic substitution with an ethylamine, substituted in position 2 with a phenyl group, which can be substituted by one or more halogen groups in the presence of a tertiary amine, as for example TEA, DIEA and the like.

(e) by means of Fmoc strategy, incorporating a unit of $N^\omega$-Fmoc-amino acid of general structure

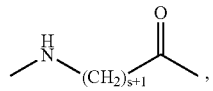

where s is 1 to 9, as for example $N^\gamma$-Fmoc-4-aminobutiric acid, $N^\epsilon$-Fmoc-6-aminohexanoic acid or $N^\omega$-Fmoc-10-aminodecanoic acid and the like.

(f) eliminating the Fmoc group with usual reactants in peptide synthesis.

(g) alkylating or acylating the generated free amino function if necessary;

(h) releasing the compound from the resin in the acid medium.

According to a third embodiment, a compound of Formula (I) can be prepared, where $R_1$ is amino, hydroxyl or thiol, all of them substituted with

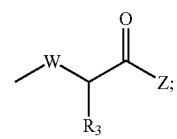

Z is amino, hydroxyl or thiol, all of them substituted or not with aliphatic or cyclic groups;

W is a bond;

$R_3$ is

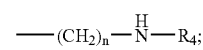

n can range between 1 and 10;

$R_4$ is H or an aliphatic or cyclic group;

$R_2$ is H or an alkyl, aryl, aralkyl or acyl group;

in accordance with a process comprising the following sequential steps:

(a) by means of Fmoc strategy, incorporating a unit of $N^\alpha$-Fmoc-amino acid of general structure

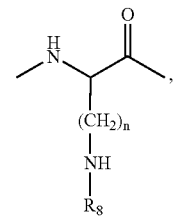

where $R_8$ is a protective group protecting the amino group, as for example Boc, Mtt and the like, and n is 1 to 10, as for example $N^\alpha$-Fmoc-$N^\beta$-Boc-2,3-diaminopropionic acid, $N^\alpha$-Fmoc-$N^\epsilon$-Boc-lysine, $N^\alpha$-Fmoc-$N^\delta$-Boc-ornithine and the like; or where $R_8$ is a group

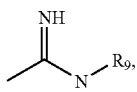

where $R_9$ is a guanidine protecting group, as for example Pmc, Pbf and the like and n is 1 to 10, as for example $N^\alpha$-Fmoc-$N^g$-Pbf-arginine, $N^\alpha$-Fmoc-$N^g$-Pmc-homoarginine and the like, on a solid support which can contain an acid-labile spacer in order to form an amide, ester or thioester bond.

(b) eliminating the Fmoc group with usual reactants in peptide synthesis.

(c) incorporating a unit of haloacetic acid by means of a coupling agent, such as a carbodiimide and the like, (d) halogen shift by nucleophilic substitution with an ethylamine, substituted in position 2 with a phenyl group, which can be substituted by one or more halogen groups in the presence of a tertiary amine as for example TEA, DIEA and the like (e) incorporating a unit of haloacetic acid by means of a coupling agent, such as a carbodiimide and the like (f) halogen shift by nucleophilic substitution with an ethylamine, substituted in position 2 with a phenyl group, which can be substituted by one or more halogen groups in presence of a tertiary amine as for example TEA, DIEA and the like (g) alkylating or acylating the generated secondary amino function, if necessary;

(h) releasing the compound from the resin in the acid medium.

According to a fourth embodiment, a compound of Formula (I) can be prepared, where $R_1$ is amino, hydroxyl or thiol, all of them substituted with

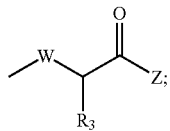

Z is amino, hydroxyl or thiol, all of them substituted or not with aliphatic or cyclic groups;

W is

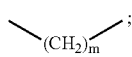

m can range between 1 and 9;

$R_3$ is H;

$R_2$ is H or an alkyl, or aryl, aralkyl or acyl group;

In accordance with a process comprising the following sequential steps:

(a) by means of Fmoc strategy, incorporating a unit of $N^\omega$-Fmoc-amino acid of general structure

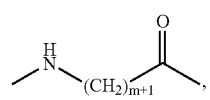

where m is 1 to 9, as for example $N^\gamma$-Fmoc-aminobutiric acid, $N^\epsilon$-Fmoc-aminohexanoic acid or $N^\omega$-Fmoc-aminodecanoic acid and the like, on a solid support which can contain an acid-labile spacer in order to form an amide, ester or thioester bond.

(b) eliminating the Fmoc group with usual reactants in peptide synthesis.

(c) incorporating a unit of haloacetic acid by means of a coupling agent, such as a carbodiimide or the like (d) halogen shift by nucleophilic substitution with an ethylamine substituted in position 2 with a phenyl group, which can be substituted by one or more halogen groups in the presence of a tertiary amine, for example TEA, DIEA and the like (e) incorporating a unit of haloacetic acid by means of a coupling agent, such as a carbodiimide and the like (f) halogen shift by nucleophilic substitution with an ethylamine, substituted in position 2 with a phenyl group, which can be substituted by one or more halogen groups in the presence of a tertiary amine as for example TEA, DIEA and the like (g) alkylating or alcylating the generated secondary amino function if necessary;

(h) releasing the compound from the resin in the acid medium.

According to a fifth embodiment, a compound of Formula (I) can be prepared, where $R_1$ is amino, hydroxyl or thiol, all of them substituted or not with aliphatic or cyclic groups;

$R_2$ is

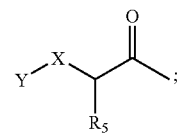

$R_5$ is H;

X is

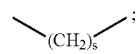

s is 1 to 9;

Y is amino substituted with a group

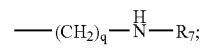

q is 1 to 9;

$R_7$ is H or an aliphatic or cyclic group;

according to a process comprising the following sequential steps:

(a) incorporating a unit of haloacetic acid by means of a coupling agent, such as a carbodiimide and the like, on a solid support which can contain an acid-labile spacer to form an amide, ester or thioester bond, (b) halogen shift by nucleophilic substitution with an ethylamine, substituted in position 2 with a phenyl group, which can be substituted by one or more halogen groups, in the presence of a tertiary amine, as for example TEA, DIEA, and the like.
(c) incorporating a unit of haloacetic acid by means of a coupling agent, such as a carbodiimide and the like.
(d) halogen shift by nucleophilic substitution with an ethylamine, substituted in position 2 with a phenyl group, which can be substituted by one or more halogen groups in the presence of a tertiary amine, as for example TEA, DIEA and the like.
(e) incorporating a unit of a ω-haloacid, with a linear structure with s methylenes, where s can range between 1 and 9, by means of a coupling agent, such as a carbodiimide and the like.
(f) halogen shift by nucleophilic substitution with a primary aliphatic or cyclic amine, with a linear structure with q methylenes, where q can range between 1 and 9 and where $q+s \leqq 12$, in the presence of a tertiary amine, for example TEA, DIEA and the like.
(g) alkylating or alcylating the generated free amino function if necessary;
(h) releasing the compound from the resin in the acid medium.

The biological activity of the compounds of Formula (I) according to the invention was determined in inflammatory pain models in animals. The compounds are able to attenuate pain caused by the subcutaneous injection of a capsaicin solution into the extremity of a mouse. Likewise, the compounds of Formula (I) show activity decreasing thermal nociception assessed in the hot-plate test. However, these compounds do not affect the mechanical nociception determined in the Von Frey hair test.

Analyses carried out in order to determine the action mechanism of the compounds of Formula (I) show that they prevent the entrance of the calcium cation into the rachideal ganglion primary neurons exposed to capsaicin, suggesting an action at a level of a vanilloid receptor The results obtained in the inflammatory pain models in animals seem to indicate that the compounds of Formula (I) are strong candidates for constituting a new generation of analgesics.

Accordingly, the compounds of Formula (I) can be suitable for treating diseases and pathological alterations such as the pain sensation; especially that occurring as a response to different harmful stimuli (mechanical, chemical and thermal) which cause acute and chronic inflammatory pain, as well as that derived from lesions in the nervous system causing neuropathic pain.

The compounds according to the invention can form part of different types of compositions for their application in the body of a mammal, preferably a human being. In this respect, the invention provides a composition comprising compounds of Formula (I). In a particular embodiment, said composition is a pharmaceutical composition, whereas in another particular embodiment said composition is a cosmetic composition.

The pharmaceutical composition provided by this invention comprises a therapeutically effective amount of at least one compound of Formula (I), together with at least one pharmaceutically acceptable excipient.

The compounds of Formula (I) of the invention can be administered in order to treat algesia by any means producing the contact of the compounds with the site of action thereof within the body of a mammal, preferably a human being.

The therapeutically effective amount of the compounds and/or pharmaceutical compositions according to the invention, which must be administered in order to treat a pathological condition, as well as the dosage thereof, will depend on many factors, including the age, condition of the patient, the severity of the alteration or disorder, the administration route and frequency, and the particular compounds of Formula (I) to be used.

Pharmaceutical compositions containing the compounds of Formula (I) can be presented in any administration form, for example, solid or liquid, and can be administered by any suitable route, for example, orally; parenterally, rectally or topically, to which end they will include the pharmaceutically acceptable excipients necessary for formulating the desired administration form. One review of the different pharmaceutical forms of administration of medicinal products and of the excipients necessary for the obtainment thereof can be found, for example, in the "Tratado de Farmacia Galénica" (*Treaty of Galenic Pharmacy*), C. Fauli i Trillo, 1993, Luzán 5, S. A. Ediciones, Madrid.

Therefore, an additional aspect of this invention refers to the use of the compounds of Formula (I) in the production of a medicinal product for attenuating the nervous activity of the primary sensory neurons involved in the pain sensations, evoked by applying exogenous chemical substances or by thermal stimuli or by endogenous release of substances by the inflamed tissues, or in the production of a medicinal product which inhibits the ion channels which are activated by exogenous chemical substances or by thermal stimuli or by inflammation mediators leading to the pain sensation or by the lesion of a nerve leading to neuropathic pain.

More specifically, the invention refers to the use of compounds of Formula (I) in the production of a medicinal product for treating diseases and pathological alterations mediated by the activation of nociceptors, for example, pain sensation in response to a harmful stimulus.

The invention furthermore provides a method for treating diseases and pathological alterations in a patient which are mediated by the nociceptor sensitization, for example the pain sensation mediated by excessive activation thereof in response to different harmful stimuli, for example, mechanical, chemical and thermal, or pro-algesic mediators, which comprises administering to said patient suffering from said disease or pathological alteration a therapeutically effective amount of at least one compound of Formula (I), preferably in the form of a pharmaceutical composition containing it.

The cosmetic composition provided by this invention comprises a cosmetically effective amount of at least one compound of Formula (I) together with at least one cosmetically acceptable excipient or adjuvant.

The compounds of the invention can be administered in cosmetic compositions for relieving, reducing, attenuating or alleviating the pain or skin irritation caused by poorly aggressive thermal (for example, exposure to the sun), mechanical (for example, depilation, shaving) or chemical stimuli. The cosmetic composition of the invention can be presented in any suitable form in order to allow the contact of the compound with the site of action thereof on the body of the mammal on which it is applied.

The amount of the compounds of Formula (I) to be administered depends on many factors, among which are the pain or irritation level caused by the thermal, mechanical or chemical stimulus and the compounds of Formula (I) to be used.

The cosmetic compositions containing the compounds of Formula (I) can be presented in any administration form, for example, solid or liquid, and can be administered by any suitable route, preferably topically, to which end they will include cosmetically acceptable excipients or adjuvants suitable for the presentation form of the cosmetic composition.

According to a particular embodiment, the cosmetic composition, comprising at least one compound of Formula (I), is an after-sun product, for example, an after-sun cream, ointment or lotion, suitable for reducing and relieving discomfort caused by sun burns due to sun exposure.

According to another particular embodiment, the cosmetic composition of the invention is an after-shave product, for example, an after-shave cream, balm or lotion, which is suitable for relieving, reducing, attenuating or alleviating the pain or skin irritation caused by mechanical stimuli (shaving). In another particular embodiment, the cosmetic composition of-the invention is an-after-depilation product, for example, after-depilation cream, ointment or lotion, which is suitable for relieving, reducing, attenuating or alleviating the pain or skin irritation caused by depilation. A review of the different presentation forms of cosmetic compositions and of the excipients or adjuvants necessary for obtainment thereof can be found, for example, in "Cosmetologia Teórico-Práctica" (*Theoretical-practical cosmetology*), Prof. A. del Pozo, published by Consejo General de Colegios Oficiales de Farmacéuticos (*General Council of Official Associations of Pharmacists*), 3$^{rd}$ Edition, 1985.

Therefore, an additional aspect of this invention refers to the use of the compounds of Formula (I) in the production of a cosmetic composition suitable for relieving, reducing, attenuating or alleviating the pain or skin irritation caused by thermal, mechanical or chemical stimuli.

The invention also provides a cosmetic method for relieving, reducing, attenuating or alleviating the pain or skin irritation caused by thermal, mechanical or chemical stimuli in a mammal; preferably a human being, which comprises administering an effective amount of the compounds of Formula (I) to said mammal, preferably in the form of a cosmetic composition containing them.

EXAMPLES

The following examples serve to illustrate the nature of the present invention and they should not be considered in the limiting sense thereof.

General Methods

Chemical Synthesis

All the synthetic processes are carried out in polypropylene syringes provided with porous polyethylene discs. All the reactants and solvents have quality for synthesis and are used without any additional treatment. The solvents and soluble reactants are eliminated by suction. The elimination of the Fmoc group is carried out with piperidine-DMF (2:8, v/v) (1×1 minute, 1×5 minutes; 5 mL/g resin) (8). The washings between the deprotection, coupling, and again, deprotection steps have been carried out with DMF (3×1 minute) using 10 mL solvent/g resin each time. The washes immediately prior and subsequent to the incorporation of the amines are carried out with 10% DMSO in DMF (3×1 minute). The coupling reactions have been carried out with 3 mL solvent/g resin. The control of the couplings is carried out by means of the ninhydrin test (18) or chloranil test (19), as required, and amine incorporation test by means of the chloranil test. All the synthetic transformations and washes have been carried out at 25° C.

The HPLC chromatographic analysis is carried out on a Shimadzu equipment (Kyoto, Japan), by using a reverse phase column thermostatized at 30° C. (250×4.0 mm, Kromasil $C_8$, 5 µm, Akzo Nobel, Sweden). Elution is carried out by means of an acetonitrile gradient (+0.07% TFA) in water (+0.1% TFA) at a flow rate of 1 mL/min and the detection is carried out at 220 nm.

Biological Activity

Biological activity of the compounds was tested in animal models of nociception and inflammatory pain was caused by a chemical irritant.

A 52° C. hot plate test was used as a nociception test, where the latency time to paw withdrawal or jump of the animal was monitored. The compounds were intraperitoneally administered to mice at a dose of 10 mg/Kg. The behavioral test was carried out at 30, 60 and 120 minutes after the administration of the compounds.

The analgesic activity of the products was determined by assessing their effect in the acute inflammatory pain model caused by subcutaneous administration of the capsaicin irritant. Administration of this vanilloid causes a neurogenic inflammation in animals with acute painful burning sensation resulting in thermal and mechanical hyperalgesia. The behavioral latency time to paw lick after intraperitoneal administration of the compounds to mice at different doses was monitored.

Abbreviations

Abbreviations used for the amino acids follow the rules of the Biochemical Nomenclature Committee of the IUPAC-IUB specified in *Eur. J. Biochem.* (1984) 138, 9–37, and in *J. Biol. Chem.* (1989) 264, 633–673.

Ahx, aminohexanoic acid; AM, 2-[4-aminomethyl-(2,4-dimethoxyphenyl) phenoxyacetic acid; Boc, tert-butyloxycarbonyl; DCM; dichloromethane; DIEA, diisopropylethylamine; DIPCDI, N,N'-diisopropylcarbodiimide; DIEA, N,N-diisopropylethylamine; DMF, N,N-dimethylformamide; DMSO, dimethylsulfoxide, ES-MS, electrospray mass spectrometry; Fmoc, fluorenylmethoxycarbonyl; HPLC, high performance liquid chromatography; MALDI-TOF-MS, matrix-assisted laser desorption ionization-time-of-flight-mass-spectrometry; MBHA, p-methylbenzhydrylamine resin; MeCN, acetonitrile; MeOH, methanol; Mtt, 4-methyltrityl (4-methyltriphenylmethyl); NMDA, N-methyl-D-aspartate; PAL, 5-(4-aminomethyl-3,5-dimethoxyphenoxy) valeric acid, Pbf, 2,2,4,6,7-pentamethyldihydrobenzofuran-5-sulphonyl; Pmc, 2,2,5,7,8-pentamethylchroman-6-sulphonyl; TEA, triethylamine; TFA, trifluoroacetic acid; TRPV1, vanilloid receptor.

Example 1

Chemical Synthesis

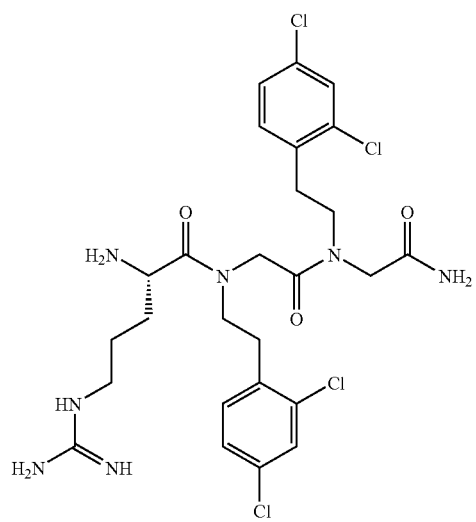

297.7 mg of chloroacetic acid (3.15 mmol, 5 equiv) are incorporated on the AM-MBHA resin (1.0 g, 0.63 mmol) in the presence of DIPCDI (485.0 µL, 3.15 mmol, 5 equiv) using DMF as a solvent. The resin is subsequently treated twice for 3 hours with 2,4-dichlorophenylethylamine (475.2 µL, 3.15 mmol, 5 equiv) in the presence of TEA (439.0 µL, 3.15 mmol, 5 equiv) using 10% DMSO in DMF as a solvent. The two previous steps and the washes between the steps are repeated in order to incorporate the second unit of N-(2,4-dichlorophenethyl)glycine. After its incorporation, Fmoc-L-Arg(Pmc)-OH (1.043 g, 1.57 mmol, 2.5 equiv) is coupled on the resin for 1 hour using DIPCDI (242.4 µL, 1.57 mmol, 2.5 equiv) and HOBt (236.25 mg, 1.57 mmol, 2.5 equiv) and using DMF as a solvent. The Fmoc group is deprotected as described in the general methods, the resin is washed with DMF (5×1 minute), DCM (4×1 minute), diethyl ether (4×1 minute) and is vacuum-dried.

725 mg of the resin are treated with TFA-H$_2$O (95:5) (7 mL, 1×120 minutes). The filtrates as well as the resultants from washing the resin with TFA-H$_2$O (95:5) are collected, and evaporated to dryness.

The total yield of synthesis and separation of the compound from the resin was 100%. The HPLC analysis in a 5 to 85% MeCN gradient (+0.07% TFA) in H$_2$O (+0.1% TFA) indicated a purity exceeding 85% and its molecular weight was determined by ES-MS [(M+H)$^+_{theoretical}$634.08, (M+H)$^+_{exp}$634.1].

Biological Activity

The results obtained in the nociception test show an increase in the latency to the first response in the animals treated with the compound with regard to those treated with a carrier: 11.5±2 s (carrier), 20±4 s (treated, 30 minutes after), 18±3 s (treated, 60 minutes after) and 18±4 s (treated, 120 minutes after). This increase in the latency is indicative of an anti-nociceptive activity of the compound in vivo.

The results obtained in the analgesic activity test show that in mice treated with carrier solution, the behavioral latency time (paw lick) was 20±5 s. This latency increased to 90±10 s with a dose of 2 mg/Kg of the compound, to 190±50 s at 5 mg/Kg, and 250±40 s at 10 mg/Kg. Similarly, the duration of the behavioral response decreased as the dose of the compound increased.

Taken together, these results indicate that this compound has an anti-nociceptive and analgesic activity in vivo, probably due to the modulation of the TRPV1 thermoreceptor, an integrator of harmful thermal and chemical stimuli. In this respect, the compound blocked an 80% of the nervous activity caused by capsaicin in afferent nerve fibers from the knee of the rat, and inhibited an 85% of the entrance of calcium cation stimulated by capsaicin in primary trigeminal neuronal cultures.

Example 2

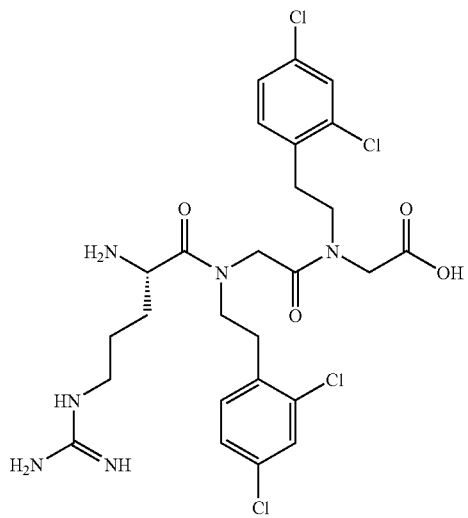

76 mg of chloroacetic acid (0.78 mmol, 1 equiv) dissolved in DCM (10 mL/g resin) to which 337 µL of DIEA (0.26 mmol, 0.33 equiv) have been added, are incorporated on the dry 2-chlorotrityl resin (0.563 g, 0.78 mmol). It is stirred for 5 minutes, after which 225 µL of DIEA (0.52 mmol, 0.67 equiv) are added. It is reacted for 40 minutes. The remaining chloride groups are blocked by means of treatment with 450 µL of MeOH (0.8 mL/g resin).

All the processes of incorporation of the following units 2,4-dichlorophenethylamine, chloroacetic acid, 2,4-dichlorophenethylamine and Fmoc-L-Arg(Pmc)-OH described in example 1 are repeated with the same amounts of reactants and reaction times. The amino terminal Fmoc group is deprotected as is described in the general methods, the resin is washed with DMF (5×1 minute), DCM (4×1 minute), diethyl ether (4×1 minute) and is vacuum-dried.

The total yield of synthesis and separation of the compound from the resin was 100%. The HPLC analysis in a 5 to 85% MeCN gradient (+0.07% TFA) in H$_2$O (+0.1% TFA) indicated a purity exceeding 83% and its molecular weight was determined by ES-MS [(M+H)$^+_{theoretical}$635.07, (M+H)$^+_{exp}$634.8].

Example 3

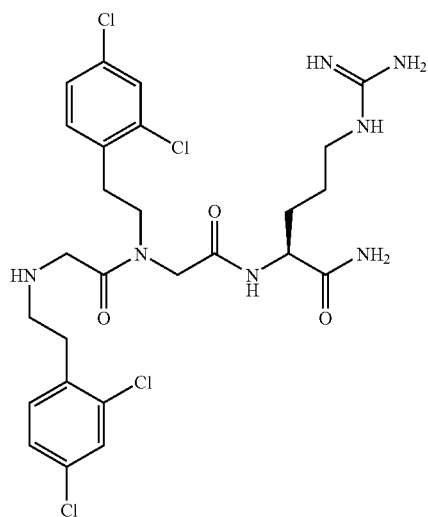

Fmoc-L-Arg(Pmc)-OH (755.6 mg, 1.14 mmol, 3 equiv) is incorporated on the AM-MBHA resin (0.5 g, 0.38 mmol) for 1 hour in the presence of DIPCDI (175.4 μL, 1.14 mmol, 3 equiv) and HOBt (174.4 mg, 1.14 mmol, 3 equiv) using DMF as a solvent. The Fmoc group is deprotected as is described in the general methods. Subsequently, chloroacetic acid (179.6 mg, 1.9 mmol, 5 equiv) is incorporated in presence of DIPCDI (292.4 μL, 1.9 mmol, 5 equiv) for 30 minutes, after which the resin is treated twice for 3 hours with 2,4-dichlorophenethylamine (286.6 μL, 1.9 mmol, 5 equiv) in the presence of TEA (263.4 μL, 1.9 mmol, 5 equiv) using 10% DMSO in DMF as a solvent. The two previous steps and the washings between the steps are repeated in order to incorporate the second unit of N-(2,4-dichlorophenethyl)glycine. Finally, the resin is washed with DMF (5×1 minute), DCM (4×1 minute), diethyl ether (4×1 minute) and is vacuum-dried. The resin is treated with TFA-H$_2$O (95:5) (7 mL, 1×120 minutes). The filtrates, as well as the resultants of washing the resin with TFA-H$_2$O (95:5) are collected and evaporated to dryness.

The total yield of synthesis and separation of the compound from the resin was 100%. The HPLC analysis in a 5 to 85% MeCN gradient (+0.07% TFA) in H$_2$O (+0.1% TFA) indicated a purity exceeding 88% and its molecular weight was determined by MALDI-TOF-MS [(M+H)$^+_{theoretial}$634.08, (M+H)$^+_{exp}$634.6].

Example 4

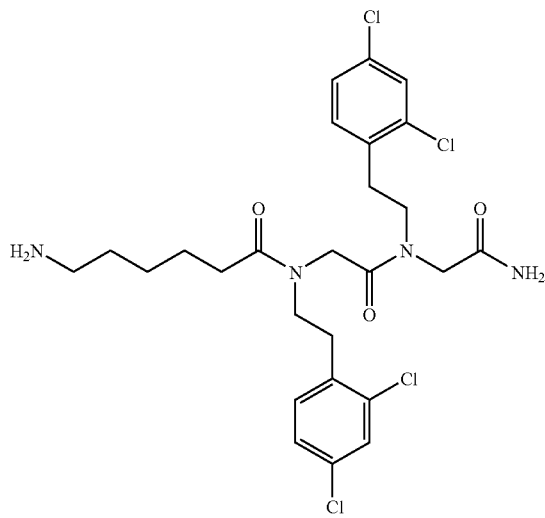

372.3 mg of chloroacetic acid (3.94 mmol, 5 equiv) are incorporated on the AM-MBHA resin (0.62 g, 0.787 mmol) in the presence of DIPCDI (606.4 μL, 3.94 mmol, 5 equiv) using DMF as a solvent. The resin is subsequently treated twice for 3 hours with 2,4-dichlorophenethylamine (475.5 μL, 3.15 mmol, 4 equiv) in the presence of TEA (439.3 μL, 3.15 mmol, 4 equiv) using 10% DMSO in DMF as a solvent. The two previous steps and the washings between the steps are repeated in order to incorporate the second unit of N-(2,4-dichlorophenethyl)glycine. After its incorporation, Fmoc-Ahx-OH (696.20 g, 1.97 mmol, 2.5 equiv) is coupled on the resin for 1 hour using DIPCDI (303.2 μL, 1.97 mmol, 2.5 equiv) and HOBt (295.5 mg, 1.97 mmol, 2.5 equiv) and using DMF as a solvent. The Fmoc group is deprotected as is described in the general methods, the resin is washed with DMF (5×1 minute), DCM (4×1 minute), diethyl ether (4×1 minute) and is vacuum-dried. The resin is treated with TFA-H$_2$O (95:5) (11 mL, 1×120 minutes). The filtrates as well as the resultants from washing the resin with TFA-H$_2$O (95:5) are collected and evaporated to dryness.

The total yield of synthesis and separation of the compound from the resin was 100%. The HPLC analysis in a 40 to 70% MeCN gradient (+0.07% TFA) in H$_2$O (+0.1% TFA) indicated a purity exceeding 77% and its molecular weight was determined by ES-MS [(M+H)$^+_{theoretical}$613.05, (M+H)$^+_{exp}$612.8].

Example 5

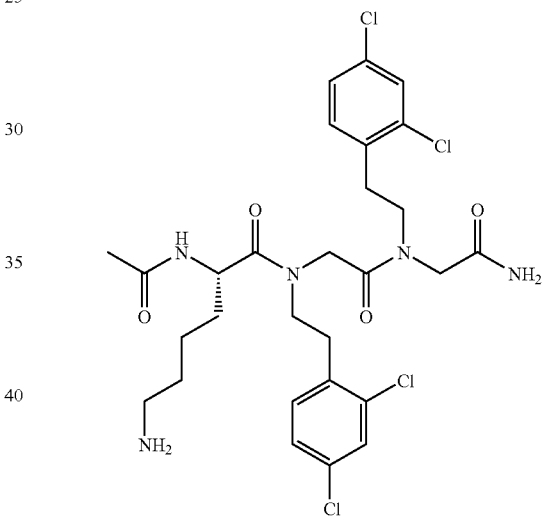

The compound of the example 5 is obtained following the same synthesis protocol as in example 1 (solvents, excess amounts and reactants), but incorporating Fmoc-L-Lys(Boc)-OH (738 mg, 1.57 mmol) instead of Fmoc-L-Arg(Pmc)-OH on the N-(2,4-dichlorophenethyl)glycinyl-N-(2,4-dichlorophenethyl)glycinyl-AM-MBHA resin, and subsequently treating it for 30 minutes with acetic anhydride (756.2 μL, 15.75 mmol) in the presence of DIEA (1.37 mL, 15.75 mmol) using DMF as a solvent. The resin is washed with DMF (5×1 minute), DCM (4×1 minute), diethyl ether (4×1 minute) and is vacuum-dried. The resin is treated with TFA-H$_2$O (95:5) (5.5 mL, 1×120 minutes). The filtrates as well as the resultants from washing the resin with TFA-H$_2$O (95:5) are collected and evaporated to dryness.

The total yield of synthesis and separation of the compound from the resin was 100%. The HPLC analysis in a 35 to 65% MeCN gradient (+0.07% TFA) in H$_2$O (+0.1% TFA) indicated a purity exceeding 71% and its molecular weight was determined by ES-MS [(M+H)$^+_{theoretical}$648.09, (M+H)$^+_{exp}$647.8].

Example 6

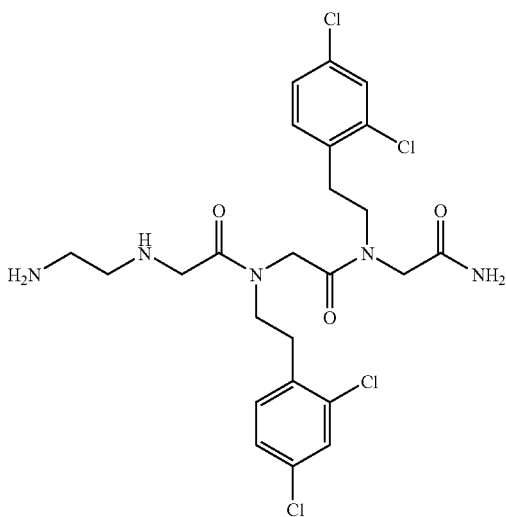

363.8 mg of chloroacetic acid (3.85 mmol, 5 equiv) are incorporated on the AM-MBHA resin (0.606 g, 0.770 mmol) in the presence of DIPCDI (592.5 µL, 3.85 mmol, 5 equiv) using DMF as a solvent. The resin is subsequently treated twice for 3 hours with 2,4-dichlorophenethylamine (464.6 µL, 3.08 mmol, 4 equiv) in the presence of TEA (429.3 µL, 3.08 mmol, 4 equiv) using 10% DMSO in DMF as a solvent. The two previous steps and the washings between the steps are repeated in order to incorporate the second unit of N-(2,4-dichlorophenethyl)glycine. After its incorporation, chloroacetic acid (361.7 mg, 3.85 mmol, 5 equiv) is coupled on the resin for 30 minutes in the presence of DIPCDI (592.5 µL, 3.85 mmol, 5 equiv) using DMF as a solvent and is subsequently treated twice for 3 hours with ethylendiamine (257.4 mL, 3.85 mmol, 5 equiv) using 10% DMSO in DMF as a solvent. The resin is washed with DMF (5×1 minute), DCM (4×1 minute), diethyl ether (4×1 minute) and is vacuum-dried. The resin is treated with TFA-H$_2$O (95:5) (10 mL, 1×120 minutes). The filtrates as well as the resultants from washing the resin with TFA-H$_2$O (95:5) are collected and evaporated to dryness.

The total yield of synthesis and separation of the compound from the resin was 100%. The HPLC analysis in a 5 to 85% MeCN gradient (+0.07% TFA) in H$_2$O (+0.1% TFA) indicated a purity exceeding 87% and its molecular weight was determined by ES-MS [(M+H)$^+_{theoretical}$ 578.05, (M+H)$^+_{exp}$ 577.7, (M+Na)$^+_{theoretical}$ 600.03, (M+H)$^+_{exp}$ 600.0].

LITERATURE

1. Fields, H. L. (1987) *Pain* (McGraw-Hill), New York.
2. Baranauskas, G. and Nistri, A. (1998) *Prog. Neurobiol.* 54, 349–365.
3. Karlsten, R. and Gordh, T. (1997) *Drugs Aging* 11, 398–412.
4. González, P., Cabello, P., Germany, A., Norris, B. and Contreras, E. (1997) *Eur. J. Pharmacol.* 332, 257–262.
5. Lipton, S. A. and Rosenburg, P. A. (1994). *New Engl. J. Med.* 330, 613–622.
6. Stewart J. M. and Young J. D. (1984) *Solid Phase Peptide Synthesis*, 2nd edition, Pierce Chemical Company, Rockford, Ill.
7. Bodanzsky M. and Bodanzsky A. (1984) *The practice of Peptide Synthesis*, Springer Verlag, N.Y.
8. Lloyd-Williams, P., Albericio, F. and Giralt, E. (1997) *Chemical Approaches to the Synthesis of Peptides and Proteins*. CRC, Boca Raton (Fla., USA).
9. Zuckermann R. N., Kerr J. M., Kent S. B. H., Moos W. H. (1992) *J. Am. Chem. Soc.* 14, 10646–10647.
10. Figliozzi G. M., Goldsmith R., Banville S. C., Zuckermann R. N. (1996) *Method Enzymol.* 267, 437–447.
11. Greene T. W. (1981) *Protective groups in organic synthesis*, John Wiley & Sons, New York.
12. Atherton et al. (1984) *Solid Phase Peptide Synthesis: A practical approach*, IRL Press Oxford University.
13. Matsueda G. R., Stewart J. M. (1981) *Peptides* 2, 45–50
14. Barlos K., Gatos D., Kallitsis J., Papaphotiu G., Sotiriu P., Wenqing Y., Schäfer W. (1989) *Tetrahedron Lett.* 30, 3943–3946 and 3947–3951.
15. Albericio F., Kneib-Cordonier N., Biancalana S., Gera L., Masada R. I., Hudson D., Barany G. (1990) *J. Org. Chem.* 55, 3730–3743.
16. Rink H. (1987) *Tetrahedron Lett.* 28, 3787–3790.
17. Wang, S. S. (1973) *J. Am. Chem. Soc.* 95, 1328–1333.
18. Kaiser, E., Colescott R. L., Bossinger C. D., Cook P. I. (1970) *Anal. Biochem.* 34, 594–598.
19. Christensen T. (1979) *Acta Chem. Scand. B.* 33, 763–766.

The invention claimed is:

1. A compound of general Formula (I)

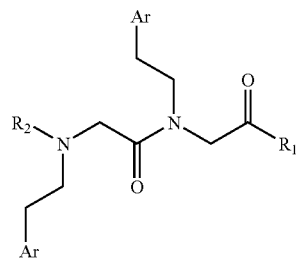

including its stereoisomers and mixtures thereof and the pharmaceutically acceptable salts thereof, wherein Ar is a phenyl group substituted with at least one halogen group;

R$_1$ is amino, hydroxyl or thiol, each of which may be substituted with

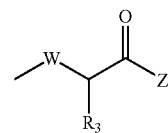

or aliphatic groups or cyclic groups;

Z is amino, hydroxyl or thiol, each of which may be substituted with aliphatic or cyclic groups;

W is a bond or

m ranges between 1 and 9;
$R_3$ is H or

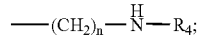

n ranges between 1 and 10;
$R_4$ is H, or an aliphatic or cyclic group;
$R_2$ is H or an alkyl, aryl, aralkyl or acyl group or

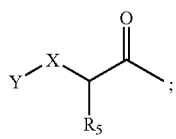

X is a bond or

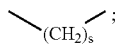

s ranges between 1 and 9:
$R_5$ is H or

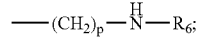

p ranges between 1 and 10;
$R_6$ is H, or an aliphatic or cyclic group;
Y is amino, which may be substituted with

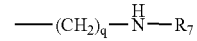

or an alkyl, aryl, aralkyl or acyl group;
q ranges between 1 and 9;
and $R_7$ is H, or an aliphatic or cyclic group.

2. A compound according to claim 1, where Ar is a 2,4-dichlorosubstituted phenyl group.

3. A compound according to claim 1, where n and p are, independently from one another, 1 to 5, and where m, q and s are, independently from one another, 1 to 4.

4. A compound according to claim 1, where $R_4$ and $R_6$ are, independently from one another, H or

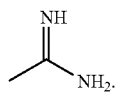

5. A compound according to claim 1, where $R_1$ is amino or hydroxyl, $R_2$ is

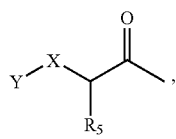

X is a bond, $R_5$ is

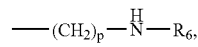

$R_6$ is H, and Y is unsubstituted or acetylated amino.

6. A compound according to claim 5, where $R_1$ is amino, Y is unsubstituted amino and p is 4.

7. A compound according to claim 5, where $R_1$ is hydroxyl, Y is unsubstituted amino and p is 4.

8. A compound according to claim 5 where $R_1$ is amino, Y is acetylated amino and p is 4.

9. A compound according to claim 5 where $R_1$ is hydroxyl, Y is acetylated amino and p is 4.

10. A compound according to claim 1 where $R_1$ is amino or hydroxyl, $R_2$ is

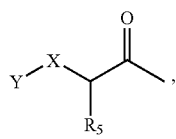

X is a bond, $R_5$ is

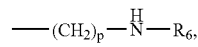

$R_6$ is

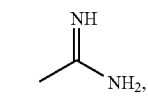

and Y is unsubstituted or acetylated amino.

11. A compound according to claim 10 where $R_1$ is amino, Y is unsubstituted amino and p is 3.

12. A compound according to claim 10 where $R_1$ is amino, Y is acetylated amino and p is 3.

13. A compound according to claim 10 where $R_1$ is hydroxyl, Y is unsubstituted amino and p is 3.

14. A compound according to claim 10 where $R_1$ is hydroxyl, Y is acetylated amino and p is 3.

15. A compound according to claim 1 where $R_1$ is amino or hydroxyl, $R_2$ is

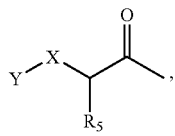

X is

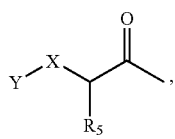

$R_5$ is H, and Y is unsubstituted amino.

16. A compound according to claim 15 where $R_1$ is amino and s is 4.

17. A compound according to claim 15 where $R_1$ is hydroxyl and s is 4.

18. A compound according to claim 1 where $R_1$ is amino or hydroxyl, $R_2$ is

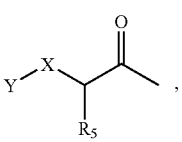

X is a bond, $R_5$ is H, Y is amino substituted with a group

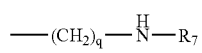

and $R_7$ is H.

19. A compound according to claim 18 where $R_1$ is amino and q is 2.

20. A compound according to claim 18 where $R_1$ is hydroxyl and q is 2.

21. A compound according to claim 1 where $R_1$ is amino substituted with

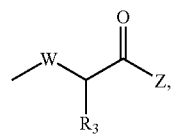

$R_2$ is H or an alkyl, aryl, aralkyl or acyl group, W is a bond, $R_3$ is

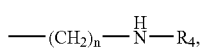

Z is amino or hydroxyl, and $R_4$ is

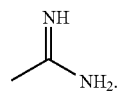

22. A compound according to claim 21 where $R_2$ is H, Z is amino and n is 3.

23. A compound according to claim 21 where $R_2$ is H, Z is hydroxyl and n is 3.

24. A compound according to claim 4 where $R_1$ is amino substituted with

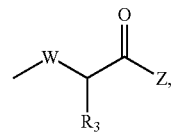

$R_2$ is H or an alkyl, aryl, aralkyl or acyl group, W is a bond, $R_3$ is

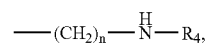

Z is amino or hydroxyl, and $R_4$ is H.

25. A compound according to claim 24 where $R_2$ is H, Z is amino and n is 4.

26. A compound according to claim 24 where $R_2$ is H, Z is hydroxyl and n is 4.

27. A method for obtaining a compound of Formula (I), according to claims 5 or 10 comprising the following sequential steps:
  (a) incorporating a unit of haloacetic acid using a coupling agent on a solid support which can contain an acid-labile spacer to form an amide or ester bond, or using nucleophilic substitution on a polymeric support containing a halogen group as a leaving group with the formation of an ester bond;
  (b) halogen shifting by nucleophilic substitution with 2,4-dichlorophenethylamine, in the presence of a tertiary amine;
  (c) incorporating a unit of haloacetic acid with a coupling agent;
  (d) halogen shifting by nucleophilic substitution with 2,4-dichlorophenethylamine, in the presence of a tertiary amine;
  (e) using an Fmoc strategy, incorporating a unit of $N^\alpha$-Fmoc-amino acid of general structure

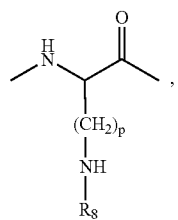

where $R_8$ is an amino protecting the group and p is 1 to 10 or where $R_8$ is a group

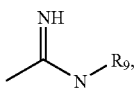

where $R_9$ is a guanidine protecting group and p is 1 to 10;
(f) eliminating the Fmoc group;
(g) alkylating or acylating the generated free amino function if necessary; and
(h) releasing the compound from the solid support in acid medium.

28. A method according to claim 27 for obtaining a compound of Formula

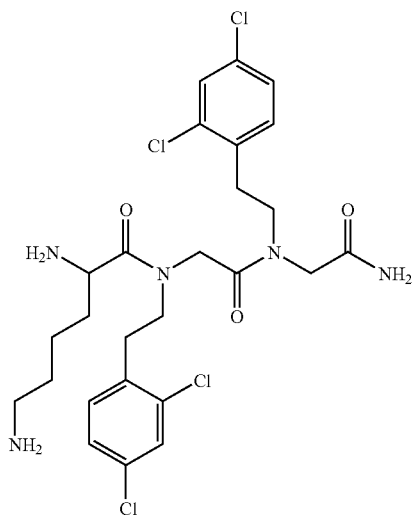

where the solid support contains an acid-labile spacer which forms an amide bond, the haloacetic acid is chloroacetic acid and wherein $N^\alpha$-Fmoc-amino acid is protected L-lysine.

29. A method according to claim 27 for obtaining a compound of Formula

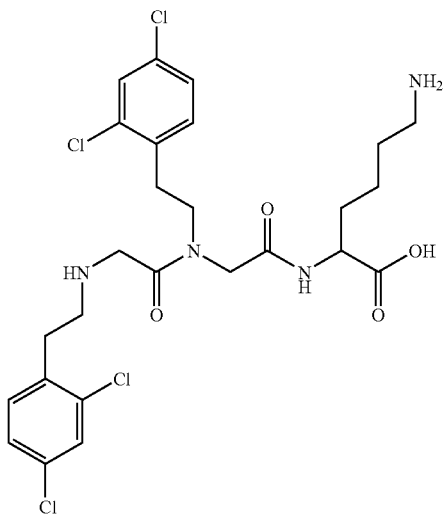

where the solid support contains halogen as a leaving group, so as to permit incorporation of the haloacetic acid by means of a nucleophilic substitution with the formation of an ester bond, or where the solid support has an acid-labile spacer which forms an ester bond, wherein the haloacetic acid is chloroacetic acid and wherein $N^\alpha$-Fmoc-amino acid is protected L-lysine.

30. A method according to claim 27 for obtaining a compound of Formula

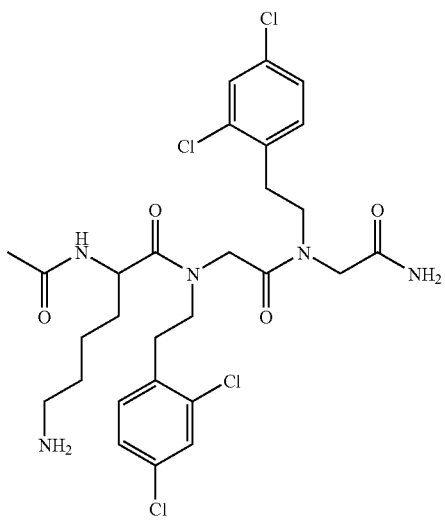

where the solid support contains an acid-labile spacer which forms an amide bond, wherein the haloacetic acid is chloroacetic acid, the $N^\alpha$-Fmoc-amino acid is protected L-lysine, and the amino group generated after deprotection of the Fmoc is acetylated.

31. A method according to claim 27 for obtaining a compound of Formula

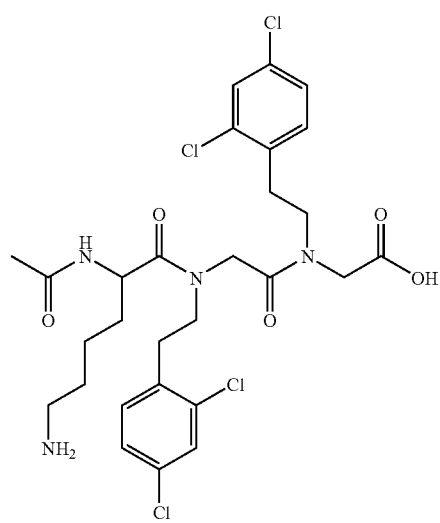

where the solid support contains halogen as a leaving group, so as to permit incorporation of the haloacetic acid by means of a nucleophilic substitution with the formation of an ester bond, or where the solid support has an acid-labile space which forms an ester bond, wherein the haloacetic acid is chloroacetic acid, the N$^\alpha$-Fmoc-amino acid is protected L-lysine and the amino group generated after deprotection of the Fmoc is acetylated.

32. A method according to claim 27 for obtaining a compound of Formula

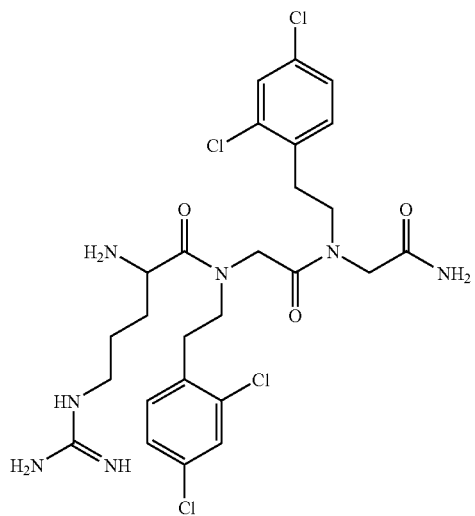

where the solid support contains an acid-labile spacer which forms an amide bond, wherein the haloacetic acid is chloroacetic acid and wherein the N$^\alpha$-Fmoc-amino acid is protected L-arginine.

33. A method according to claim 27 for obtaining a compound of Formula

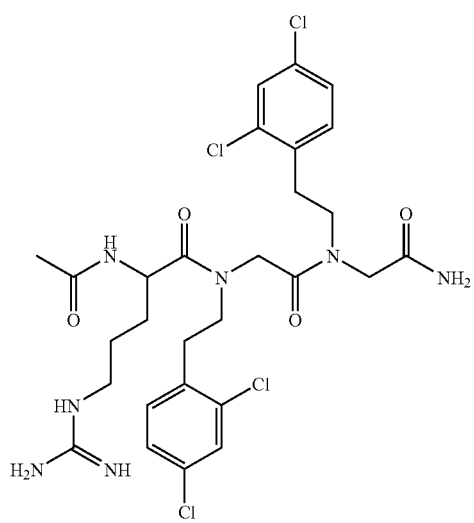

where the solid support contains an acid-labile spacer which forms an amide bond, wherein the haloacetic acid is chloroacetic acid, the N$^\alpha$-Fmoc-amino acid is protected L-arginine and wherein the amino group generated after deprotection of the Fmoc is acetylated.

34. A method according to claim 27 for obtaining a compound of Formula

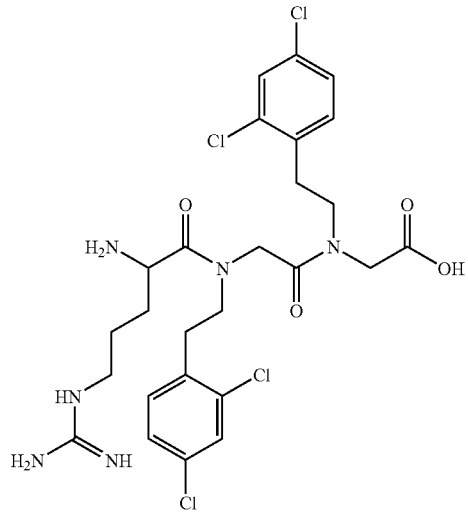

where the solid support contains halogen as a leaving group so as to permit the incorporation of the haloacetic acid by means of a nucleophilic substitution with the formation of an ester bond, or where the solid support has an acid-labile spacer which forms an ester bond, the haloacetic acid is chloroacetic acid and wherein the N$^\alpha$-Fmoc-amino acid is protected L-arginine.

35. A method according to claim 27 for obtaining a compound of Formula

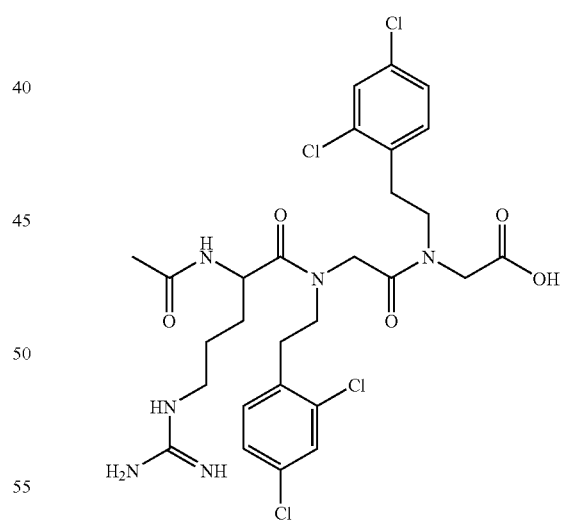

where the solid support contains halogen as a leaving group, so as to permit the incorporation of the haloacetic acid by means of a nucleophilic substitution with the formation of an ester bond, or where the solid support has an acid-labile spacer which forms an ester bond, the haloacetic acid is chloroacetic acid, the N$^\alpha$-Fmoc-amino acid is protected L-arginine and wherein the amino group generated after deprotection of the Fmoc is acetylated.

36. A method for obtaining a compound of Formula (I) according to claim 15 comprising the following sequential steps:
   (a) incorporating a unit of haloacetic acid using a coupling agent, on a solid support which contains an acid-labile spacer in order to form an amide or ester bond, or by means of a nucleophilic substitution on a polymeric support containing a halogen group as a leaving group with the formation of an ester bond;
   (b) halogen shifting by nucleophilic substitution with 2,4-dichlorophenethylamine, in the presence of a tertiary amine;
   (c) incorporating a unit of haloacetic acid using a coupling agent;
   (d) halogen shifting by nucleophilic substitution with 2,4-dichlorophenethylamine, in the presence of a tertiary amine;
   (e) using an Fmoc strategy, incorporating a unit of $N^\alpha$-Fmoc-amino acid of general structure.

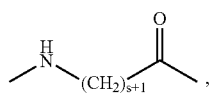

where s is 1 to 9,
   (f) eliminating the Fmoc group; and
   (g) releasing the compound from the solid support in the acid medium.

37. A method according to claim 36 for obtaining a compound of Formula

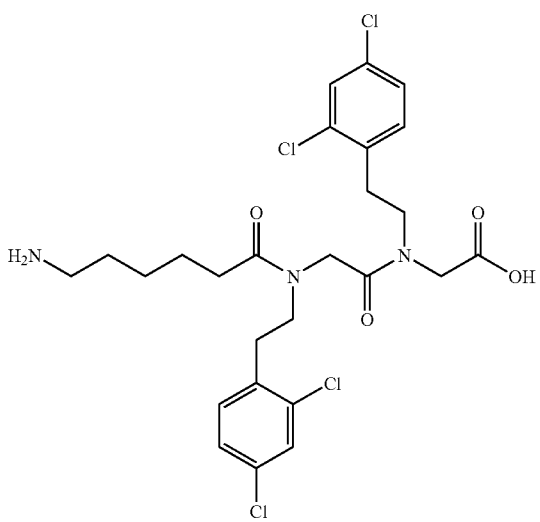

where the solid support contains an acid-labile spacer which forms an amide bond, wherein the haloacetic acid is chloroacetic acid and wherein the $N^\omega$-Fmoc-amino acid is protected 6-aminohexanoic acid.

38. A method according to claim 36 for obtaining a compound of Formula

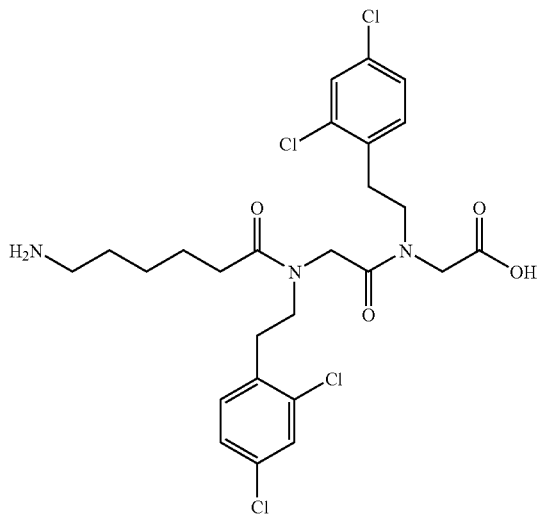

(I) according to claim 17, based on a solid-phase strategy, where the solid support contains halogen as a leaving group, which permits the incorporation of the haloacetic acid by means of a nucleophilic substitution with the formation of an ester bond, or where the solid support has an acid-labile spacer which forms an ester bond, wherein the haloacetic acid is chloroacetic acid and wherein the $N^\omega$-Fmoc-amino acid is protected 6-aminohexanoic acid.

39. A method for obtaining a compound of Formula (I) according to claim 18 comprising the following sequential steps:
   (a) incorporating a unit of haloacetic acid using a coupling agent on a solid support containing an acid-labile spacer in order to form an amide or ester bond, or by means of a nucleophilic substitution on a polymeric support containing halogen group as a leaving group with the formation of an ester bond;
   (b) halogen shifting by nucleophilic substitution with 2,4-dichlorophenethylamine, in the presence of a tertiary amine;
   (c) incorporating a unit of haloacetic acid using a coupling agent;
   (d) halogen shifting by nucleophilic substitution with 2,4-dichlorophenethylamine, in the presence of a tertiary amine;
   (e) incorporating a unit of a ω-haloacid, with a linear structure with s methylenes, where s ranges between 1 and 9, using a coupling agent;
   (f) halogen shifting by nucleophilic substitution with a primary aliphatic or cyclic amine, with a linear structure with q methylenes, where q ranges between 1 and 9 and where $q+s \leq 12$, in the presence of a tertiary amine;
   (g) alkylating or acylating the generated free amino function if necessary; and
   (h) releasing the compound from the solid support in acid medium.

40. A method according to claim 39 for obtaining a compound of Formula

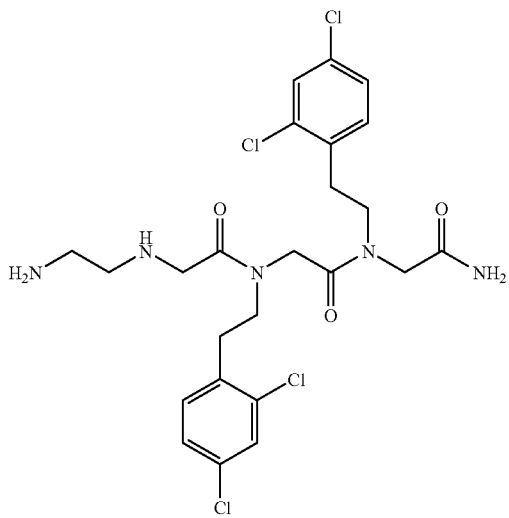

where the solid support contains an acid-labile spacer which forms an amide bond, wherein the haloacetic acid and ω-haloacid are chloroacetic acid and where in the primary amine is 1,2-ethylenediamine.

41. A method according to claim 39 for obtaining a compound of Formula

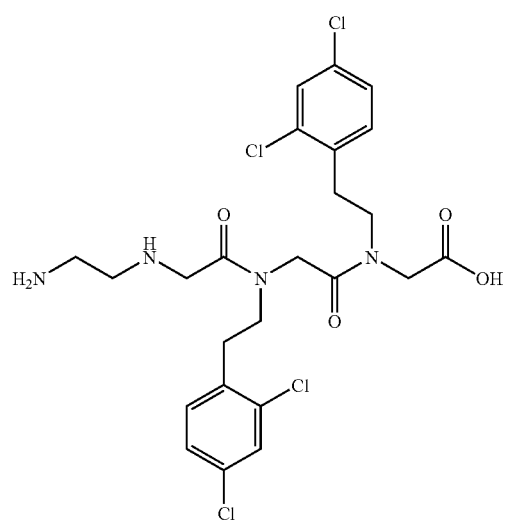

where the solid support contains halogen as a leaving group, so as to permit incorporation of the haloacetic acid using a nucleophilic substitution with the formation of an ester bond, or where the solid support has an acid-labile spacer which forms an ester bond, wherein the haloacetic acid and ω-haloacid are chloroacetic acid and wherein the primary amine is 1,2-ethylenediamine.

42. A method for obtaining a compound of Formula (I) according to claims 21 or 24 comprising the following sequential steps:
(a) using a Fmoc strategy, incorporating a unit of $N^\alpha$-Fmoc-amino acid of general structure

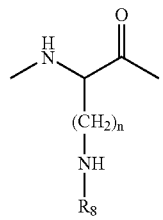

where $R_8$ is an amino protecting group and n is 1 to 10, or where $R_8$ is a group

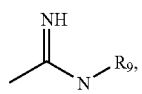

where $R_9$ is a guanidine protecting group and n is 1 to 10 on a solid support containing an acid-labile spacer in order to form an amide or ester bond, or using a nucleophilic substitution on a polymeric support containing halogen group as a leaving group with the formation of an ester bond;
(a) eliminating the Fmoc group;
(b) incorporating a unit of haloacetic acid using a coupling agent
(c) halogen shifting by nucleophilic substitution with 2,4-dichlorophenethylamine, in the presence of a tertiary amine;
(d) incorporating a unit of haloacetic acid of using a coupling agent;
(e) halogen shifting by nucleophilic substitution with 2,4-dichlorophenethylamine, in the presence of a tertiary amine;
(f) alkylating or acylating the generated secondary amino function if necessary; and
(g) releasing the compound from the solid support in the acid medium.

43. A method according to claim 42 for obtaining a compound of Formula

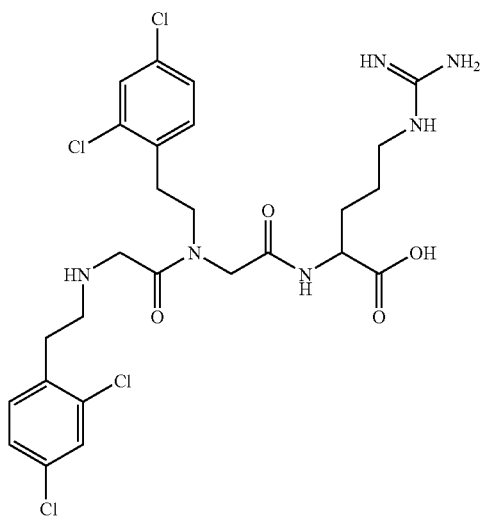

where the solid support contains an acid-labile spacer which forms an amide bond, wherein the haloacetic acid is chloroacetic acid, and wherein the N^α-Fmoc-amino acid is protected L-arginine.

44. A method according to claim 42 for obtaining a compound of Formula

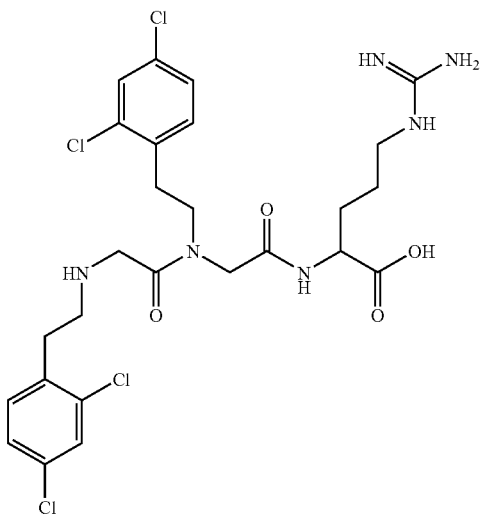

where the solid support contains halogen as a leaving group, so as to permit incorporation of the haloacetic acid using a nucleophilic substitution which forms an ester bond, or where the solid support has an acid-labile spacer which forms an ester bond, wherein the haloacetic acid is chloroacetic acid, and wherein N^α-Fmoc-amino acid is protected L-arginine.

45. A method according to claim 42 for obtaining a compound of Formula

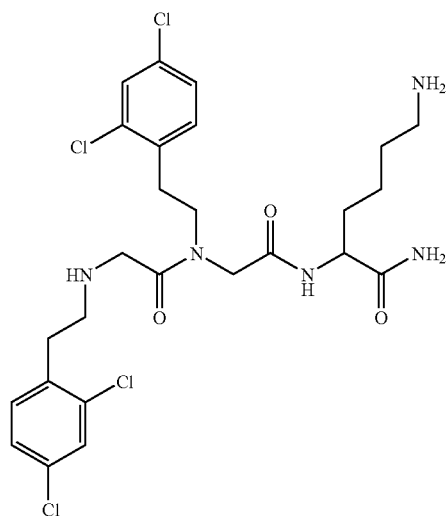

where the solid support contains an acid-labile spacer forms which forms an amide bond, wherein the haloacetic acid is chloroacetic acid, and wherein the N^α-Fmoc-amino acid is protected L-lysine.

46. A method according to claim 42 for obtaining a compound of Formula

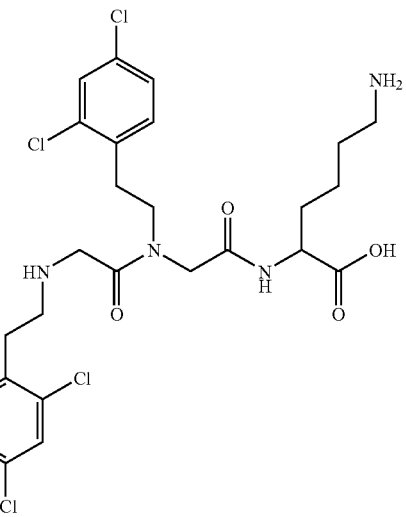

where the solid support contains halogen as a leaving group, so as to permit incorporation of the haloacetic acid using a nucleophilic substitution with the formation of an ester bond, or where the solid support has an acid-labile spacer which forms an ester bond, wherein the haloacetic acid is chloroacetic acid, and wherein the N^α-Fmoc-amino acid is protected L-lysine.

47. A composition comprising at least one compound of Formula (I) according to claim 1.

48. A pharmaceutical composition comprising a therapeutically effective amount of at least one compound of Formula (I) according to claim 1 and, at least, one pharmaceutically acceptable excipient.

49. A cosmetic composition comprising a cosmetically effective amount of at least one compound of Formula (I) according to claim 1, and at least one cosmetically acceptable excipient or adjuvant.

50. A cosmetic composition according to claim 49, selected from among an after-sun product, a pre-shave product, an after-shave product, a pre-depilation product and an after-depilation product.

51. A method for attenuating the nervous activity of primary senson neurons involved in pain sensations evoked by applying exogenous chemical substances or by thermal stimuli or by endogenous release of substances by inflamed tissues or by a nerve lesion in a subject in need of such attenuation comprising administering to said subject an effective amount of a compound of general Formula (I)

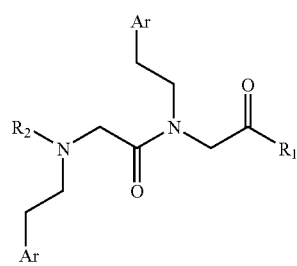

including its stereoisomers and mixtures thereof and the pharmaceutically acceptable salts thereof, wherein Ar is a phenyl group substituted with at least one halogen group;

$R_1$ is amino, hydroxyl or thiol, each of which may be substituted with

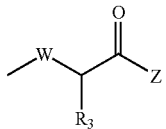

or aliphatic groups or cyclic groups;

Z is amino, hydroxyl or thiol, each of which may be substituted with aliphatic or cyclic groups;

W is a bond or

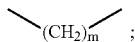

m ranges between 1 and 9;

$R_3$ is H or

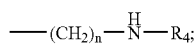

n ranges between 1 and 10;

$R_4$ is H, or an aliphatic or cyclic group;

$R_2$ is H or an alkyl, aryl, aralkyl or acyl group or

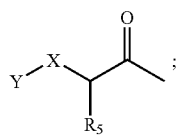

X is a bond or

s ranges between 1 and 9:

$R_5$ is H or

p ranges between 1 and 10;

$R_6$ is H, or an aliphatic or cyclic group;

Y is amino, which may be substituted with

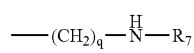

or an alkyl, aryl, aralkyl or acyl group;

q ranges between 1 and 9;

and $R_7$ is H, or an aliphatic or cyclic group;

or a pharmaceutically acceptable salt thereof.

52. A method according to claim 51 wherein such attenuation of the nervous activity of primary senson neurons involved in pain sensations is achieved by inhibition of the ion channels which are activated by exogenous chemical substances or by thermal stimuli or by inflammation mediators leading to pain sensation.

53. A method of treating pathological disorders and diseases mediated by sensitization of nociceptors or a nerve lesion, in a subject in need thereof comprising administering to said subject an effective amount of a compound of general Formula (I)

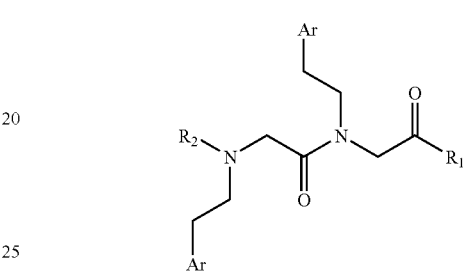

including its stereoisomers and mixtures thereof and the pharmaceutically acceptable salts thereof, wherein Ar is a phenyl group substituted with at least one halogen group;

$R_1$ is amino, hydroxyl or thiol, each of which may be substituted with

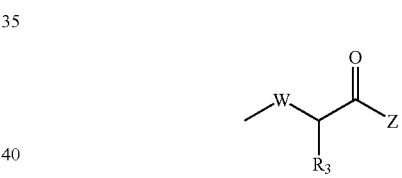

or aliphatic groups or cyclic groups;

Z is amino, hydroxyl or thiol, each of which may be substituted with aliphatic or cyclic groups;

W is a bond or

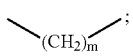

m ranges between 1 and 9;

$R_3$ is H or n ranges between 1 and 10;

$R_4$ is H, or an aliphatic or cyclic group;

$R_2$ is H or an alkyl, aryl, aralkyl or acyl group or

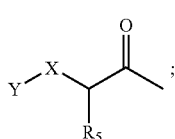

X is a bond or

s ranges between 1 and 9:
R$_5$ is H or

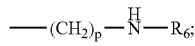

p ranges between 1 and 10;
R$_6$ is H, or an aliphatic or cyclic group;
Y is amino, which may be substituted with

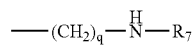

or an alkyl, aryl, aralkyl or acyl group;
q ranges between 1 and 9;
and R$_7$ is H, or an aliphatic or cyclic group;
or a pharmaceutically acceptable salt thereof.

54. A method according to claim 53 wherein such pathological disorder or disease is pain.

55. A method according to claim 53 wherein such pathological disorder or disease is thermal hyperalgesia.

56. A method according to claim 53 wherein such pathological disorder or disease is inflammatory pain, neuropathic pain and neurogenic inflammation.

57. A method according to claim 56 wherein such inflammatory pain is burns, osteoarthritis, rheumatoid arthritis, fibromyalgia, myofacial and back pain.

58. A method according to claim 53 wherein such pathological disorder or disease is visceral pelvic pain, abdominal pain and bladder pain.

59. A method according to claim 56 wherein such neuropathic pain is trigeminal neuralgia, diabetic neuropathy, herpetic neuropathy and traumatic nerve lesion.

60. A method according to claim 56 wherein such inflammatory pain or neuropathic pain is associated to cancerous tumors.

61. A cosmetic composition comprising a cosmetically effective mount of at least one compound of Formula (I) according to claim 1, and at least one cosmetically acceptable excipient or adjuvant.

62. A cosmetic composition according to claim 61, selected from among an after-sun product, a pre-shave product, an after-shave product, a pre-depilation product and an after-depilation product.

63. A method of relieving, reducing, attenuating or alleviating pain or skin irritation caused by thermal stimuli, mechanical stimuli, chemical stimuli or thermal hyperalgesia in a subject in need thereof, comprising administering to said subject an effective amount of a compound of general Formula (I)

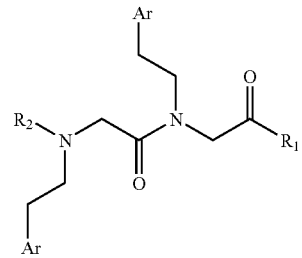

including its stereoisomers and mixtures thereof and the pharmaceutically acceptable salts thereof, wherein
Ar is a phenyl group substituted with at least one halogen group;
R$_1$ is amino, hydroxyl or thiol, each of which may be substituted with

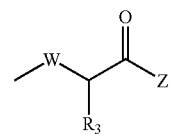

or aliphatic groups or cyclic groups;
Z is amino, hydroxyl or thiol, each of which may be substituted with aliphatic or cyclic groups;
W is a bond or

m ranges between 1 and 9;
R$_3$ is H or

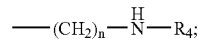

n ranges between 1 and 10;
R$_4$ is H, or an aliphatic or cyclic group;
R$_2$ is H or an alkyl, aryl, aralkyl or acyl group or

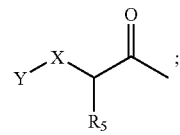

X is a bond or

s ranges between 1 and 9:

$R_5$ is H or
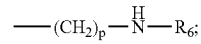
p ranges between 1 and 10;
$R_6$ is H, or an aliphatic or cyclic group;
Y is amino, which may be substituted with
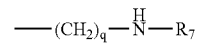
or an alkyl, aryl, aralkyl or acyl group;
q ranges between 1 and 9;
and $R_7$ is H, or an aliphatic or cyclic group;
or a cosmetically acceptable salt thereof.
* * * * *